US010751310B2

(12) United States Patent
Freeman et al.

(10) Patent No.: US 10,751,310 B2
(45) Date of Patent: Aug. 25, 2020

(54) PREVENTION, TREATMENT AND REVERSAL OF DISEASE USING THERAPEUTICALLY EFFECTIVE AMOUNTS OF DICARBOXYLIC ACID COMPOUNDS

(71) Applicant: UNIVERSITY OF PITTSBURGH—OF THE COMMONWEALTH SYSTEM OF HIGHER EDUCATION, Pittsburgh, PA (US)

(72) Inventors: Bruce A. Freeman, Pittsburgh, PA (US); Francisco J. Schopfer, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 16/081,791

(22) PCT Filed: Mar. 2, 2017

(86) PCT No.: PCT/US2017/020477
§ 371 (c)(1),
(2) Date: Aug. 31, 2018

(87) PCT Pub. No.: WO2017/151938
PCT Pub. Date: Sep. 8, 2017

(65) Prior Publication Data
US 2019/0091186 A1    Mar. 28, 2019

Related U.S. Application Data

(60) Provisional application No. 62/303,960, filed on Mar. 4, 2016.

(51) Int. Cl.
*A61K 31/194* (2006.01)
*A61K 9/00* (2006.01)
*C07C 323/52* (2006.01)
*A61K 31/225* (2006.01)

(52) U.S. Cl.
CPC .......... *A61K 31/194* (2013.01); *A61K 9/0073* (2013.01); *C07C 323/52* (2013.01); *A61K 9/0019* (2013.01); *A61K 9/0034* (2013.01); *A61K 9/0053* (2013.01); *A61K 31/225* (2013.01)

(58) Field of Classification Search
CPC .. C07C 323/52; A61K 9/0019; A61K 9/0034; A61K 31/225; A61K 9/0073; A61K 31/194; A61K 9/0053
See application file for complete search history.

(56) References Cited

U.S. PATENT DOCUMENTS

| | | | |
|---|---|---|---|
| 3,527,789 A | 9/1970 | Payne | |
| 4,166,913 A | 9/1979 | Kesling, Jr. et al. | |
| 6,528,499 B1 * | 3/2003 | Kozikowski | C07C 59/347 514/574 |
| 8,324,277 B2 | 12/2012 | Freeman | |
| 8,735,449 B2 | 5/2014 | Freeman | |
| 9,066,902 B2 | 6/2015 | Freeman et al. | |
| 9,186,408 B2 | 11/2015 | Freeman et al. | |
| 9,700,534 B2 | 7/2017 | Freeman et al. | |
| 9,750,725 B2 | 9/2017 | Freeman et al. | |
| 10,213,417 B2 | 2/2019 | Freeman et al. | |
| 10,258,589 B2 | 4/2019 | Freeman et al. | |
| 2015/0018417 A1 | 1/2015 | Freeman et al. | |

FOREIGN PATENT DOCUMENTS

| | | |
|---|---|---|
| CN | 103705499 | 4/2014 |
| DE | 102011118462 | 5/2013 |
| GB | 1153464 | 5/1969 |
| WO | WO 2002/022627 | 3/2002 |
| WO | WO 2009/017802 | 2/2009 |
| WO | WO 2009/112455 | 9/2009 |
| WO | WO 2010/005521 | 1/2010 |
| WO | WO 2010/014889 | 2/2010 |
| WO | WO 2011/014261 | 2/2011 |
| WO | WO 2013/116753 | 8/2013 |
| WO | WO 2013/142206 | 9/2013 |
| WO | WO 2013/162924 | 10/2013 |
| WO | WO 2015/012367 | 1/2015 |

OTHER PUBLICATIONS

CAS Abstract of e-EROS Encyclopedia of Reagents for Organic Synthesis (2007), No pp. given. John Wiley & Sons, Ltd.: Chichester, UK. (Year: 2007).*
Alessandro Palmieri et al., Green Chemistry Group, School of Science and Technology, Chemistry Division, University of Camerino, Camerino, 62032, Italy .Green Chemistry (2013), 15(9), 2344-2348. "Low impact synthesis of β-nitroacrylates under fully heterogeneous conditions" (Year: 2013).*
Mohammad Rafiee et al., Studies in Basic Sciences (IASBS), Zanjan, Iran., "CEC mechanism in electrochemical oxidation of nitrocatechol-boric acid complexes", Electrochimica Acta (2011), 56(27), 9946-9952 CODEN: ELCAAV; ISSN: 0013-4686 . (Year: 2011).*
Roberto Ballini et al.,Stereoselective preparation of (E)-.vepsiln.-nitro-β,γ-unsaturated methyl esters: Amberlyst A 27, using microwave, as superior catalyst for the 1,6-conjugate addition of nitroalkanes to methyl 1,3-butadiene-1-carboxylate. (Year: 2001).*

(Continued)

*Primary Examiner* — Alexander R Pagano
*Assistant Examiner* — Ebenezer O Sackey
(74) *Attorney, Agent, or Firm* — Klarquist Sparkman, LLP

(57) ABSTRACT

Various embodiments of this invention are directed to pharmaceutical compositions and methods for treating disease. The compositions of such embodiments include dicarboxylic acid compounds containing electron withdrawing groups, alkyl esters of dicarboxylic acids containing electron withdrawing groups, or compounds of Formulae I to X. The methods of various embodiments include administering an effective amount of any of these pharmaceutical compositions to a patient in need of treatment.

37 Claims, No Drawings

(56) References Cited

OTHER PUBLICATIONS

Baker et al., "Anodic syntheses. Part XIV. The use of acetylenic components. A new synthesis of oleic acid," *Journal of the Chemical Society*, pp. 2218-2227, Dec. 30, 1955.

Cantet et al., "A new synthesis of trifluorinated compounds via 1,1-dichloro-1-alkenes in superacid," *Tetrahedron Letters*, 48(30): 5255-5260, Jul. 23, 2007.

Effenberger et al., "Selective hydrolysis of aliphatic dinitriles to monocarboxylic acids by a nitrilase from *Arabidopsis thaliana*," *Synthesis*, No. 12, pp. 1866-1872, Sep. 25, 2001.

Eliasson et al., "Aliphatic medium chain tricarboxylic acids in rat urine," *Journal of Lipid Research*, vol. 17, pp. 637-646, Nov. 30, 1976.

International Search Report and Written Opinion issued for International Application No. PCT/US2017/010477 dated Jun. 20, 2017.

Linforth et al., "2,7-dimethyl-octa-2,4-dienedioic acid a possible by-product of abscisic acid biosynthesis in the tomato," *Phytochemistry*, 26(6): 1631-1634, Dec. 30, 1987.

Tsai et al., "A novel synthesis of 1,21-heneicosanedioic acid," *The Journal of Organic Chemistry*, 45(23): 4785-4786, Nov. 30, 1980.

U.S. Appl. No. 16/239,425, filed Jan. 3, 2019.

U.S. Appl. No. 16/280,704, filed Feb. 20, 2019.

Akone et al., "2-pentenedioic acid derivatives from a soil-derived fungus *Gongorella butleri*," *Phytochemistry Letters*, vol. 10, pp. 184-188, Sep. 19, 2014.

Hon et al., "Syntheses of bifunctional compounds from cycloalkenes via ozonide intermediates," *Tetrahedron*, 53(14): 5217-5232, Apr. 7, 1997.

Supplemental Partial European Search Report issued for EPC Application No. 17760831.2 dated Dec. 10, 2019.

Xu et al., "A simple and highly efficient procedure for construction of quaternary carbons centers by tributylphosphine catalyzed bis-Michael addition," *Tetrahedron*, vol. 70, pp. 176-180, Dec. 4, 2013.

Zurcher et al., "The oxidation of 3-(1-Nitro-2-oxocycloalkyl)propanal," *elvetica Chimica Acta*, 70(7): 1937-1943, Nov. 1987 (in German with English abstract).

\* cited by examiner

PREVENTION, TREATMENT AND REVERSAL OF DISEASE USING THERAPEUTICALLY EFFECTIVE AMOUNTS OF DICARBOXYLIC ACID COMPOUNDS

CROSS REFERENCE TO RELATED APPLICATION

This is the U.S. National Stage of International Application No. PCT/US2017/020477, filed Mar. 2, 2017, which was published in English under PCT Article 21(2), which in turn claims the benefit of U.S. Provisional Application No. 62/303,960, filed Mar. 4, 2016, which is incorporated by reference herein.

ACKNOWLEDGMENT OF GOVERNMENT SUPPORT

This invention was made with government support under grant number HL058115 awarded by the National Institutes of Health. The government has certain rights in the invention.

SUMMARY

In some embodiments, a method of treating a disease comprises administering a therapeutically effective amount of a dicarboxylic acid compound containing an electron withdrawing group, an alkyl ester of dicarboxylic acid containing an electron withdrawing group, or a compound of Formulae I to X, to a subject in need thereof. In some embodiments, pharmaceutical composition comprises a therapeutically effective amount of a dicarboxylic acid compound, an alkyl ester of dicarboxylic acid, of a compound of Formulae I to X, and a pharmaceutically acceptable excipient. Various embodiments of the invention are directed to dicarboxylic acid compounds containing electron withdrawing groups, and in some embodiments such compounds may further contain alkenes associated with the electron withdrawing groups. Various embodiments of the invention are directed to alkyl esters of dicarboxylic acid compounds containing electron withdrawing groups, and in some embodiments such compounds may further contain alkenes associated with the electron withdrawing groups. Various embodiments of the invention are directed to compounds of Formulae I to X.

DETAILED DESCRIPTION

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

The term "alkyl" is used in this description to denote a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

An "alkenyl group" is as a branched or unbranched hydrocarbon group of 2 to 24 carbon atoms and structural formula containing at least one carbon-carbon double bond.

The phrase "alkynyl group" as employed here refers to a branched or unbranched hydrocarbon group of 2 to 24 carbon atoms and containing at least one carbon-carbon triple bond.

As used herein, "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. Exemplary aryl groups include but are not limited to phenyl, naphthyl, tetrahydronaphthyl, chlorophenyl, methylphenyl, methoxyphenyl, trifluoromethylphenyl, nitrophenyl, and 2,4-methoxychlorophenyl.

The term "halogen" and "halo" refers to —F, —Cl, —Br or —I.

The term "heteroatom" is meant to include oxygen (O), nitrogen (N), and sulfur (S).

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, —$CH_2CH_2CH_2CH_2CH_2CH_2OH$, and branched versions thereof.

The term "haloalkoyl," refers to an —($C_1$-$C_8$) alkyl group wherein one or more hydrogen atoms in the $C_1$-$C_8$ alkyl group is replaced with a halogen atom, which can be the same or different. Examples of haloalkyl groups include, but are not limited to, difluoromethyl, trifluoromethyl, 2,2,2-trifluoroethyl, 4-chlorobutyl, 3-bromopropylyl, pentachloroethyl, and 1,1,1-trifluoro-2-bromo-2-chloroethyl.

The term "amine or amino" refers to an —NRPRq group wherein Rp and Rq each independently refer to a hydrogen, ($C_1$-$C_8$) alkyl, ($C_1$-$C_8$) haloalkyl, and ($C_1$-$C_6$) hydroxyalkyl group.

The term "oxo" refers to a =O atom attached to a saturated or unsaturated ($C_3$-$C_8$) cyclic or a ($C_1$-$C_8$) acyclic moiety. The =O atom can be attached to a carbon, sulfur, and nitrogen atom that is part of the cyclic or acyclic moiety.

The term "heterocycle" refers to a monocyclic, bicyclic, tricyclic, or polycyclic systems, which are either unsaturated or aromatic and which contains from 1 to 4 heteroatoms, independently selected from nitrogen, oxygen and sulfur, wherein the nitrogen and sulfur heteroatoms are optionally oxidized and the nitrogen heteroatom optionally quaternized, including bicyclic, and tricyclic ring systems. The heterocycle may be attached via any heteroatom or carbon atom. Heterocycles include heteroaryls as defined above. Representative examples of heterocycles include, but are not limited to, benzoxazolyl, benzisoxazolyl, benzthiazolyl, benzimidazolyl, isoindolyl, indazolyl, benzodiazolyl, benzotriazolyl, benzoxazolyl, benzisoxazolyl, purinyl, indolyl, isoquinolinyl, quinolinyl and quinazolinyl. A heterocycle group can be unsubstituted or optionally substituted with one or more substituents.

"Heterocycloalkyl" denotes to a monocyclic or bicyclic ring system containing one or two saturated or unsaturated rings and containing at least one nitrogen, oxygen, or sulfur atom in the ring. The term "cycloalkyl" refers to a monocyclic or bicyclic ring system containing one or two saturated or unsaturated rings.

The term "haloalkyl," refers to a $C_1$-$C_8$ alkyl group wherein one or more hydrogen atoms in the $C_1$-$C_8$ alkyl group is replaced with a halogen atom, which can be the same or different. Examples of haloalkyl groups include, but are not limited to, trifluoromethyl, 2,2,2-trifluoroethyl, 4-chlorobutyl, 3-bromopropyl, pentachloroethyl, and 1,1,1-trifluoro-2-bromo-2-chloroethyl.

The term "heteroaryl" is employed here to refer to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and preferably one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The term "derivative" refers to a compound that is derived from a similar compound, or a compound that can be imagined to arise from another compound, if one or more atoms are replaced with another atom or group of atoms.

The term "biological sample" refers to tissue, cells, cellular extract, homogenized tissue extract, a mixture of one or more enzymes in a suitable physiologically acceptable carrier, such as a mixture that includes without limitation the hydroxy dehydrogenases and cyclooxygenases.

The compounds of the invention can exist in various isomeric forms, including configurational, geometric, and conformational isomers, as well as existing in various tautomeric forms, particularly those that differ in the point of attachment of a hydrogen atom. The term "isomer" is intended to encompass all isomeric forms of a compound of this invention, including tautomeric forms of the compound.

Certain compounds described here may have asymmetric centers and therefore exist in different enantiomeric and diastereomeric forms. The compounds of the invention can be in the form of an optical isomers or a diastereomers. Accordingly, the invention encompasses compounds in the form of their optical isomers, diastereoisomers and mixtures thereof, including a racemic mixture. Optical isomers of the compounds of the invention can be obtained by known techniques such as asymmetric synthesis, chiral chromatography, simulated moving bed technology or via chemical separation of stereoisomers through the employment of optically active resolving agents. Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

The term "prodrug" denotes a derivative of a compound that can hydrolyze, oxidize, or otherwise react under biological conditions, in vitro or in vivo, to provide an active compound, particularly a compound of the invention. Examples of prodrugs include, but are not limited to, derivatives and metabolites of a compound of the invention that include biohydrolyzable groups such as biohydrolyzable amides, biohydrolyzable esters, biohydrolyzable carbamates, biohydrolyzable carbonates, biohydrolyzable ureides, and biohydrolyzable phosphate analogues (e.g., monophosphate, diphosphate or triphosphate). For instance, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by BURGER'S MEDICINAL CHEMISTRY AND DRUG DISCOVERY 6th ed. (Wiley, 2001) and DESIGN AND APPLICATION OF PRODRUGS (Harwood Academic Publishers Gmbh, 1985).

As used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 100 mg means in the range of 90 mg-110 mg.

"Administering" when used in conjunction with a therapeutic means to administer a therapeutic to a patient whereby the therapeutic positively impacts the tissue to which it is targeted. Thus, as used herein, the term "administering", when used in conjunction with a compound described herein can include, but is not limited to, providing a compound described herein to a subject systemically by, for example, intravenous injection, whereby the therapeutic reaches the target tissue. "Administering" a composition may be accomplished by, for example, injection, oral administration, topical administration, or by these methods in combination with other known techniques. Administering may be self-administration, wherein the subject in need of such treatment administers a therapeutic or administering may be by a medical or other health care professional or a caretaker of the subject in need of such treatment.

The term "animal," "patient," or "subject" as used herein includes, but is not limited to, humans and non-human vertebrates such as wild, domestic and farm animals.

The term "improves" is used to convey that the present invention changes either the characteristics and/or the physical attributes of the tissue to which it is being provided, applied or administered. The term "improves" may also be used in conjunction with a diseased state such that when a diseased state is "improved" the symptoms or physical characteristics associated with the diseased state are diminished, reduced or eliminated.

The term "inhibiting" includes the administration of a compound of the present invention to prevent the onset of the symptoms, alleviate the symptoms, or eliminate the disease, condition, disorder or a symptom or symptoms thereof.

By "pharmaceutically acceptable", it is meant the carrier, diluent or excipient must be compatible with the other ingredients of the formulation and not deleterious to the recipient thereof.

As used herein, the term "therapeutic" means an agent utilized to discourage, combat, ameliorate, improve, prevent, inhibit, block or reverse an unwanted condition, disease or symptom of a patient as may be indicated by the particular embodiment. In part, embodiments of the present invention are directed to solid organ fibrosis, inflammatory disease, cardiovascular disease, renal disease, kidney failure, ischemic kidney injury, acute kidney injury (AKI), chronic kidney injury (CKI), chronic kidney disease (CKD), diabetic nephropathy, kidney fibrosis, focal segmental glomerulosclerosis (FSGS), non-alcoholic steatohepatitis (NASH), fatty liver disease, pulmonary arterial hypertension (PAH), pulmonary fibrosis, allergic airway disease, obesity, anti-adipogenic disease, type II diabetes, sickle cell disease, sickle cell crisis, idiopathic pulmonary fibrosis (IPF), inflammatory gastrointestinal disease, colitis, inflammatory bowel disease, neurodegenerative disease, amyotrophic lateral sclerosis (ALS), metabolic syndrome, neuropathy, Charcot-Marie-Tooth disease and mitochondrial related diseases.

A "therapeutically effective amount" or "effective amount" of a composition is a predetermined amount calculated to achieve the desired effect, i.e., to discourage, combat, ameliorate, improve, prevent, inhibit, block, or reverse an unwanted condition, disease or symptom of a patient as may be indicated by the particular embodiment. For example, a "therapeutically effective amount" as recited in a "method of treating" embodiment is a predetermined amount calculated to achieve the desired treatment effect, i.e., to discourage, combat, ameliorate, or improve an unwanted condition, disease or symptom. For example, a "therapeutically effective amount" as recited in a "method of preventing" embodiment is a predetermined amount calculated to achieve the desired treatment effect, i.e., to prevent or inhibit or block an unwanted condition, disease or symptom prior to its occurrence. In part, embodiments of the present invention are directed to solid organ fibrosis, inflammatory disease, cardiovascular disease, renal disease, kidney failure, ischemic kidney injury, acute kidney injury (AKI), chronic kidney injury (CKI), chronic kidney disease (CKD), diabetic nephropathy, kidney fibrosis, focal segmental glomerulosclerosis (FSGS), non-alcoholic steatohepatitis (NASH), fatty liver disease, pulmonary arterial hypertension (PAH), pulmonary fibrosis, allergic airway disease, obesity, anti-adipogenic disease, type II diabetes, sickle cell disease, sickle cell crisis, idiopathic pulmonary fibrosis (IPF), inflammatory gastrointestinal disease, colitis, inflammatory bowel disease, neurodegenerative disease, amyotrophic lateral sclerosis (ALS), metabolic syndrome, neuropathy, Charcot-Marie-Tooth disease and mitochondrial related diseases. The activity contemplated by the present methods includes both medical therapeutic and/or prophylactic treatment, as appropriate. The specific dose of a compound administered according to this invention to obtain therapeutic and/or prophylactic effects will, of course, be determined by the particular circumstances surrounding the case, including, for example, the compound administered, the route of administration, and the condition being treated. However, it will be understood that the effective amount administered will be determined by the physician in the light of the relevant circumstances including the condition to be treated, the choice of compound to be administered, and the chosen route of administration, and therefore, the dosage ranges included herein are not intended to limit the scope of the invention in any way. A therapeutically effective amount of compound of this invention is typically an amount such that when it is administered in a physiologically tolerable excipient composition, it is sufficient to achieve an effective systemic concentration or local concentration in the tissue.

The terms "treat," "treated," "treating," "ameliorate," "improve," or "promote" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms of the condition, disorder or disease; diminishment of the extent of the condition, disorder or disease; stabilization (i.e., not worsening) of the state of the condition, disorder or disease; maintain the condition, disorder or disease; delay in onset or slowing of the progression of the condition, disorder or disease; and remission (whether partial or total), whether detectable or undetectable, or enhancement or improvement of the condition, disorder or disease. Amelioration or promotion includes eliciting a clinically significant response without excessive levels of side effects.

Generally speaking, the term "tissue" refers to any aggregation of similarly specialized cells which are united in the performance of a particular function.

Various embodiments of the invention are directed to dicarboxylic acid compounds containing electron withdrawing groups, and in some embodiments such compounds may further contain alkenes associated with the electron withdrawing groups. Various embodiments of the invention are directed to alkyl esters of dicarboxylic acid compounds containing electron withdrawing groups, and in some embodiments such compounds may further contain alkenes associated with the electron withdrawing groups. Various embodiments of the invention are directed to compounds of Formulae I to X. Additional embodiments are directed to pharmaceutical compositions containing these compounds and methods for treating various diseases by administering these compounds.

The compounds of various embodiments may be of general Formulae I or II:

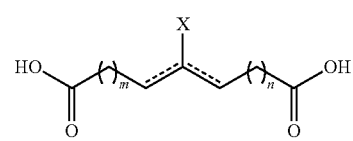

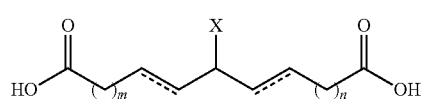

wherein X is an electron withdrawing group, each ----- can, individually, be a single or double bond, and each m and n are, independently, an integer of 1 to 10. In particular embodiments, at least one ----- depicted in Formulae I and II is a double bond. In some embodiments, both ===== depicted in Formulae I and II may be single bonds, and in other embodiments, both ===== depicted in Formulae I and II may be double bonds. In other embodiments, the compounds may be of general Formulae III and IV:

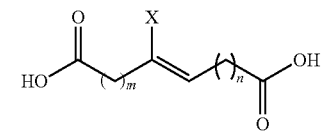

III

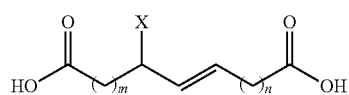

IV wherein X is an electron withdrawing group and each m and n are, independently, an integer of 1 to 10.

Further embodiments are directed to alkyl esters of the dicarboxylic acid compounds containing electron withdrawing groups such as, for example, compounds of general Formulae V and VI:

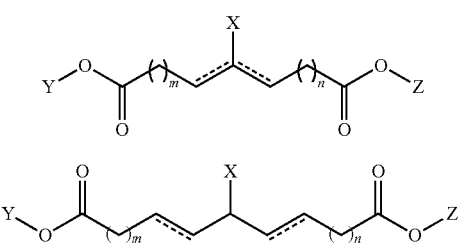

V

VI wherein X is an electron withdrawing group, each Y and Z is, individually, hydrogen or a $C_1$ to $C_{10}$ alkyl, each ===== is, individually, a single or double bond, and each m and n are, independently, absent or an integer of 1 to 10. In particular embodiments, at least one ===== depicted in Formulae V and VI is a double bond. In some embodiments, both ===== depicted in Formulae V and VI may be single bonds, and in other embodiments, both ===== depicted in Formulae V and VI may be double bonds. In some embodiments, the alkyl esters of dicarboxylic acid compounds containing electron withdrawing groups may be compounds of Formula VII and VIII:

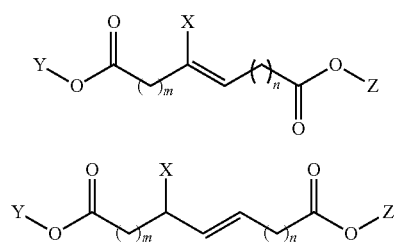

VII

VIII wherein X is an electron withdrawing group, each Y and Z is, individually, hydrogen or a $C_1$ to $C_{10}$ alkyl, and each m and n are, independently, an integer of 1 to 10. In certain embodiments, each Y and Z of the compounds of Formulae V, VI, VII, and VIII illustrated above may be methyl ($C_1$ alkyl) or ethyl ($C_2$ alkyl).

The alkylene created in by m and n in each of the compounds of Formulae I-VIII illustrated above may include carbon-carbon double bonds in addition to the double bonds depicted in Formulae III, IV, VII, and VIII or optionally present as indicated by ===== of Formulae I, II, V, and VI. For Example, the compounds of some embodiments may be of Formulae IX and X:

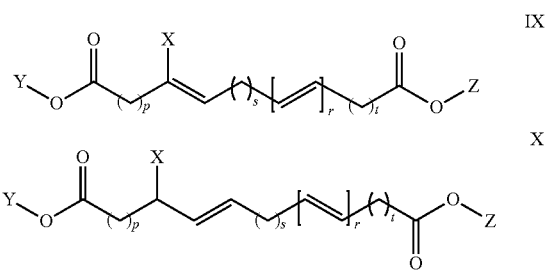

IX

X wherein X is an electron withdrawing group, each Y and Z is, individually, hydrogen or $C_1$ to $C_{10}$ alkyl, and each p and t are, independently, an integer of 1 to 10, each s is absent or an integer of 1 to 10, and each r is an integer of 1 to 5. In certain embodiments, each Y and Z of the compounds of Formulae IX and X illustrated above may be methyl ($C_1$ alkyl) or ethyl ($C_2$ alkyl).

Additional embodiments of the invention are directed to dicarboxylic acid compounds containing electron withdrawing groups further containing at least one alkene associated with the electron withdrawing group of Formulae I, III, V, VII and IX, wherein at least one alkene associated with the electron withdrawing group has been reduced the introduction of a nucleophile "A" by means of a Michael addition reaction to yield compounds of Formulae IA, IIIA, VA, VB, VIIA and IXA.

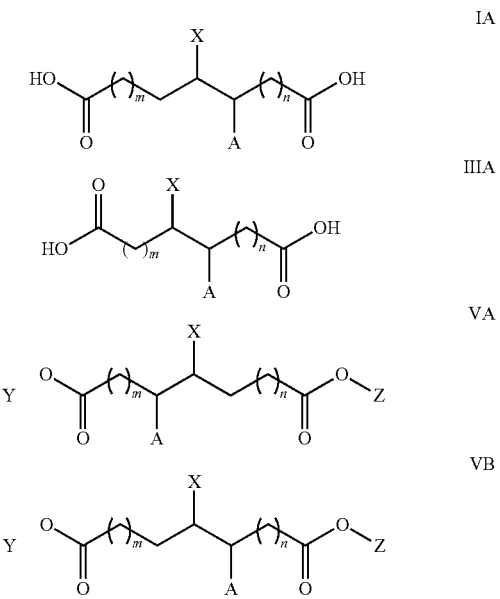

IA

IIIA

VA

VB

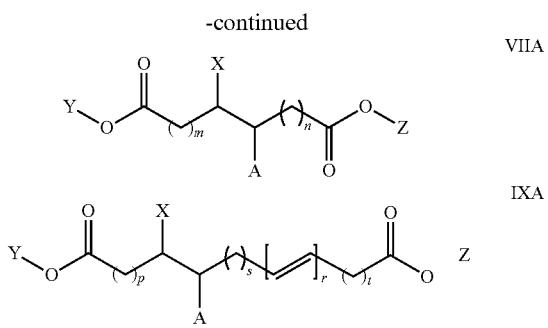

wherein X is an electron withdrawing group, A is a nucleophile, each Y and Z is, individually, hydrogen or $C_1$ to $C_{10}$ alkyl, and each m, n, p and t are, independently, an integer of 1 to 10, each s is absent or an integer of 1 to 10, and each r is an integer of 1 to 5. In certain embodiments, each Y and Z may be methyl ($C_1$ alkyl) or ethyl ($C_2$ alkyl).

It is envisioned that the compounds of Formulae IA, IIIA, VA, VB, VIIA and IXA could be useful as either prodrugs of the compounds of Formulae I, III, V, VII and IX or as active therapeutic agents themselves. If used as prodrugs, it is envisioned that the compounds of Formulae IA, IIIA, VA, VB, VIIA and IXA would metabolize in vivo after administration to a patient in need thereof to provide a therapeutically effective amount of the active agent according to Formulae I, III, V, VIII and IX.

The term "nucleophile" is recognized in the art and denotes a chemical species that donates an electron pair to an electrophile to form a chemical bond in relation to a reaction. All molecules or ions with a free pair of electrons or at least one i-bond can act as electrophiles. Nucleophiles, i.e., A, may include but are not limited to, enols, hydroxide anion, alcohols, alkoxide anions, hydrogen peroxide, carboxylate anions, hydrogen sulphide, thiols, thiolate anions, anions of thiocarboxylic acids, anions of dithiocarbonates, ammonia, azide, amines and nitriles.

The term "electron-withdrawing group" is recognized in the art and denotes the tendency of a substituent to attract valence electrons from neighbouring atoms, i.e., the substituent is electronegative with respect to neighbouring atoms. A quantification of the level of electron-withdrawing capability is given by the Hammett sigma ($\sigma$) constant (see, e.g., J. March, Advanced Organic Chemistry, McGraw Hill Book Company, New York, (1977 edition) pp. 251-259). The Hammett constant values are generally negative for electron donating groups and positive for electron withdrawing groups. For example the Hammet constant for para substituted $NH_2$ ($\sigma[P]$) is about –0.7 and the $\sigma[P]$ for a nitro group is about 0.8. Electron-withdrawing groups may include, but are not limited to, aldehyde (—COH) acyl (—COR), carbonyl (—CO), carboxylic acid (—COOH), ester (—COOR), halides (—Cl, —F, —Br, etc.), fluoromethyl (—$CF_n$) cyano (—CN), sulfonyl (—$SO_n$), sulfone (—$SO_2R$), sulfonic acid (—$SO_3H$), 1°, 2°, and 3° ammonium (—$NR^{3+}$), and nitro (—$NO_2$). In some embodiments, the electron withdrawing group may be a strong electron withdrawing group having a $\sigma$ of at least about 0.2, and in certain embodiments, the electron withdrawing group may form a dipole. For example, in particular embodiments, the electron withdrawing group may be a nitro, ammonium, or sulfonyl.

Some embodiments are directed to pharmaceutical compositions containing the compounds described above including dicarboxylic acid compounds containing electron withdrawing groups, alkyl esters of dicarboxylic acid compounds containing electron withdrawing groups and compounds of Formulae I to X. Such pharmaceutical compositions may include a dicarboxylic acid compound containing an electron withdrawing group, an alkyl ester of dicarboxylic acid containing an electron withdrawing group, a compound of Formulae I to X, or combination of compounds and a pharmaceutically acceptable carrier, excipient, or diluent.

The dicarboxylic acid compounds containing electron withdrawing groups, alkyl esters of dicarboxylic acids containing electron withdrawing groups and compounds of Formulae I to X described above may be prepared as a pharmaceutically acceptable formulation. The term "pharmaceutically acceptable" is used herein to mean that the compound is appropriate for use in a pharmaceutical product. For example, pharmaceutically acceptable cations include metallic ions and organic ions. More preferred metallic ions include, but are not limited to, appropriate alkali metal salts, alkaline earth metal salts and other physiological acceptable metal ions. Exemplary ions include aluminium, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

Isomeric and tautomeric forms of dicarboxylic acid compounds containing electron withdrawing groups, alkyl esters of dicarboxylic acids containing electron withdrawing groups or compounds of Formulae I to X of the invention as well as pharmaceutically acceptable salts of these compounds are also encompassed by the invention. Exemplary pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, .beta.-hydroxybutyric, galactaric and galacturonic acids.

Suitable pharmaceutically acceptable base addition salts used in connection with the dicarboxylic acid compounds containing electron withdrawing groups, alkyl esters of dicarboxylic acids containing electron withdrawing groups or compounds of Formulae I to X of the invention include metallic ion salts and organic ion salts. Exemplary metallic ion salts include, but are not limited to, appropriate alkali metal (group Ia) salts, alkaline earth metal (group IIa) salts and other physiological acceptable metal ions. Such salts can be made from the ions of aluminium, calcium, lithium, magnesium, potassium, sodium and zinc. Preferred organic salts can be made from tertiary amines and quaternary ammonium salts, including m part, trimethylamine, diethylamine, N,N'-dibenzylethylenediamine, chloroprocaine, choline, diethanolamine, ethylenediamine, meglumine (N-methylglucamine) and procaine. All of the above salts can be prepared by those skilled in the art by conventional means from the corresponding compound of the present invention.

In the various embodiments described above, a therapeutically effective amount of the dicarboxylic acid compound containing electron withdrawing groups, the alkyl ester of dicarboxylic acid containing electron withdrawing groups or the compound of Formulae I to X may be as a daily dose or a single dose within a range of a lower limit amount and an upper limit amount. In some embodiments, the lower limit amount is about 5 mg, about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about, 375 mg, about 400 mg, about 425 mg, about 450 mg, about 475 mg, about 500 mg, about 525 mg, about 550 mg, 600 mg, about 625 mg, about 650 mg, about 675 mg, about 700 mg, about 725 mg, about 750 mg, about 775 mg, about 800 mg, about 825 mg, about 850 mg, about 875 mg or about 900 mg. In some embodiments, the upper limit amount is about 1,000 mg, about 975 mg, about 950 mg, about 900 mg, about 875 mg, about 850 mg, about 825 mg, about 800 mg, about 775 mg, about 750 mg, about 725 mg, about 700 mg, about 675 mg, about 650 mg, about 625 mg, about 600 mg, about 575 mg, about 550 mg, about 525 mg, about 500 mg, about 475 mg, 450 mg, about 425 mg, about 400 mg, about 375 mg, about 350 mg, about 325 mg, about 300 mg, about 275 mg, about 250 mg, about 225 mg, about 200 mg, about 175 mg, about 150 mg, about 125 mg, about 100 mg, about 75 mg, or about 50 mg.

In some embodiments, the daily dose may be any range between an upper and a lower limit of ranges previously disclosed. In some embodiments, the daily dose may be from about 25 mg to less than about 1,000 mg, about 25 mg to about 1,000 mg, about 50 mg to about 975 mg, about 75 mg to about 950 mg, about 100 mg to about 925 mg, about 125 mg to about 900 mg, about 150 mg to about 875 mg, about 175 mg to about 850 mg, about 200 mg to about 825 mg, about 225 mg to about 800 mg, about 250 mg to about 775 mg, about 275 mg to about 750 mg, about 300 mg to about 725 mg, about 325 to about 700 mg, about 350 mg to about 675 mg, about 375 mg to about 650 mg, about 400 mg to about 625 mg, or about 425 mg to about 600 mg. In some embodiments, the lower limit of the range of a daily dose may be selected from 25 mg, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg. In some embodiments, the upper limit of the range of a daily dose may be selected from 1,000 mg, 975 mg, 950 mg, 925 mg, 900 mg, 875 mg, 850 mg, 825 mg, 800 mg, 775 mg, 750 mg, 825 mg, 800 mg, 775 mg, 750 mg, 725 mg, 700 mg, 675 mg, 650 mg, 625 mg, 600 mg, 575 mg, 550 mg, 525 mg, 475 mg, 450 mg, 425 mg, 400 mg, 375 mg, 350 mg, 325 mg, 300 mg or 275 mg.

In some embodiments, the daily dose as described above may be administered once per day. In some embodiments, the daily dose as described above may administered in equal amounts twice per day. In some embodiments, the daily dose as described above may administered in equal amounts three times per day. In some embodiments, the daily dose as described above may administered in equal amounts four times per day.

In some embodiments, the therapeutically effective amount of a dicarboxylic acid compound containing electron withdrawing groups, an alkyl ester of dicarboxylic acid containing electron withdrawing groups, or a compound of Formulae I to X is as a single dose, which is administered once per day or multiple times per day. For example, the above mentioned single dose may be administered as a single dose two times per day, three times per day or four times per day.

In yet other embodiments, a therapeutically effective amount of a dicarboxylic acid compound containing electron withdrawing groups, an alkyl ester of dicarboxylic acid containing electron withdrawing groups, or a compound of Formulae I to X may vary as treatment progresses. For example, the daily dose (or dosing regimen) may be increased or decreased as treatment proceeds through administration cycles, or the daily dosage may increase or decrease throughout administration.

Further embodiments are directed to methods for treating a disease by administering the compounds described above including dicarboxylic acid compounds containing electron withdrawing groups, alkyl esters of dicarboxylic acids containing electron withdrawing groups, or compounds of Formulae I to X. In some embodiments, the compounds described above may be administered as pharmaceutical compositions as described above.

Although the various compounds of the invention can be used to treat numerous disease states, in certain embodiments, disease to be treated may be solid organ fibrosis, inflammatory disease, cardiovascular disease, renal disease, kidney failure, ischemic kidney injury, acute kidney injury (AKI), chronic kidney injury (CM), chronic kidney disease (CKD), diabetic nephropathy, kidney fibrosis, focal segmental glomerulosclerosis (FSGS), non-alcoholic steatohepatitis (NASH), fatty liver disease, pulmonary arterial hypertension (PAH), pulmonary fibrosis, allergic airway disease, obesity, anti-adipogenic disease, type II diabetes, sickle cell disease, sickle cell crisis, idiopathic pulmonary fibrosis (IPF), inflammatory gastrointestinal disease, colitis, inflammatory bowel disease, neurodegenerative disease, amyotrophic lateral sclerosis (ALS), metabolic syndrome, neuropathy, Charcot-Marie-Tooth disease and mitochondrial related diseases.

The dicarboxylic acid compounds containing electron withdrawing groups, alkyl esters of dicarboxylic acids containing electron withdrawing groups, or compounds of Formulae I to X of the invention can be administered in any conventional manner by any route where they are active. Administration can be systemic or local. For example, administration can be, but is not limited to, parenteral, subcutaneous, intravenous, intramuscular, intraperitoneal, transdermal, oral, buccal, or ocular routes, or intranasally, intravaginally, by inhalation, by depot injections, or by implants. In certain embodiments, the administration may be parenteral or intravenous, all in the presence or absence of stabilizing additives that favor extended systemic uptake, tissue half-life and intracellular delivery. Thus, modes of administration for the compounds of the present invention (either alone or in combination with other pharmaceuticals) can be injectable (including short-acting, depot, implant and pellet forms injected subcutaneously or intramuscularly). In some embodiments, an injectable formulation including a dicarboxylic acid compound containing electron withdrawing groups, an alkyl ester of dicarboxylic acid containing electron withdrawing groups, or a compound of Formulae I to X may be deposited to a site of injury or inflammation, such as, for example, the site of a surgical incision or a site of inflammation due to arthroscopy, angioplasty, stent placement, by-pass surgery and so on.

In certain other embodiments, the compounds of the invention may be applied locally as a salve or lotion applied directly to an area of in need of treatment. For example, in some embodiments, a lotion or salve including a dicarboxylic acid compound containing electron withdrawing groups, an alkyl ester of dicarboxylic acid containing electron withdrawing groups, or a compound of Formulae I to X of the invention may be prepared and applied to a burn, radiation burn, site of dermal disorder, edema, arthritic joint or the like.

Various embodiments of the invention are also directed to a method for administering dicarboxylic acid compounds containing electron withdrawing groups, alkyl esters of dicarboxylic acids containing electron withdrawing groups, or compounds of Formulae I to X. Specific modes of administration may vary and may depend on the indication. The selection of the specific route of administration and the dose regimen may be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician). Those skilled in the art will appreciate that dosages may be determined with guidance, for example, from Goodman & Goldman's The Pharmacological Basis of Therapeutics, Ninth Edition (1996), Appendix II, pp. 1707-1711 or from Goodman & Goldman's The Pharmacological Basis of Therapeutics, Tenth Edition (2001), Appendix II, pp. 475-493 both of which are hereby incorporated by reference in their entireties. With respect to conventional prenylation enzyme inhibitors, guidance may be obtained from art-recognized dosage amounts as described, for example, by J. E. Karp, et al., Blood, 97(11):3361-3369 (2001) and A. A. Adjei, et al., Cancer Research, 60:1871-1877 (2000) hereby incorporated by reference in its entirety.

Further embodiments are directed to pharmaceutical compositions containing a dicarboxylic acid compound containing electron withdrawing groups, an alkyl ester of dicarboxylic acid containing electron withdrawing groups, or a compound of Formulae I to X that are useful for treating above mentioned diseases. In certain embodiments, such pharmaceutical compositions may contain a dicarboxylic acid compound containing electron withdrawing groups, an alkyl ester of dicarboxylic acid containing electron withdrawing groups, or a compound of Formulae I to X in effective amount and a pharmaceutically acceptable excipient, carrier, or diluent.

In some embodiments, a pharmaceutical composition includes sufficient amount of a dicarboxylic acid compound containing electron withdrawing groups, an alkyl ester of dicarboxylic acid containing electron withdrawing groups, or a compound of Formulae I to X to provide about 5 mg to less than about 450 mg, about 10 mg to about 450 mg, about 25 mg to less than 450 mg, about 25 mg to about 425 mg, about 25 mg to about 400 mg, about 25 mg to about 375 mg, about 25 mg to about 350 mg, about 25 mg to about 325 mg, about 25 mg to about 300 mg, about 25 mg to about 275 mg, about 25 mg to about 250 mg, about 25 mg to about 225 mg, about 25 mg to about 200 mg, about 25 mg to about 175 mg, or about 25 mg to about 150 mg. In some embodiments, the daily dose may be from about 50 mg to about 450 mg, about 75 mg to about 450 mg, about 100 mg to about 450 mg, about 150 mg to about 450 mg, about 175 mg to about 450 mg, about 200 mg to about 450 mg, about 225 mg to about 450 mg, about 250 mg to about 450 mg or about 275 mg to about 450 mg.

Pharmaceutical formulations containing dicarboxylic acid compounds containing electron withdrawing groups, alkyl esters of dicarboxylic acids containing electron withdrawing groups, or compounds of Formulae I to X of the above invention and a suitable carrier can be in various forms including, but not limited to, solids, solutions, powders, fluid emulsions, fluid suspensions, semi-solids, and dry powders. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, antioxidants, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Oilman's, The Pharmaceutical Basis of Therapeutics*, 6th Edition, MacMillan Publishing Co., New York (1980) both of which are hereby incorporated by reference in their entireties can be consulted.

The dicarboxylic acid compounds containing electron withdrawing groups, alkyl esters of dicarboxylic acids containing electron withdrawing groups, or compounds of Formulae I to X of the present invention can be formulated for parenteral or intravenous administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids diluents such as oleic acid find use in the preparation of injectables. Additional fatty acids diluents that may be useful in embodiments of the invention include, for example, one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethyleneglycerol fatty ester, polyoxyethylene fatty alcohol ether, polyethoxylated sterol, polyethoxylated castor oil, polyethoxylated vegetable oil, and the like. In some embodiments, the fatty acid diluent may be a mixture of fatty acids. In some embodiments, the fatty acid may be a fatty acid ester, a sugar ester of fatty acid, a glyceride of fatty acid, or an ethoxylated fatty acid ester, and in other embodiments, the fatty acid diluent may be a fatty alcohol such as, for example, stearyl alcohol, lauryl alcohol, palmityl alcohol, palmitolyl acid, cetyl alcohol, capryl alcohol, caprylyl alcohol, oleyl alcohol, linolenyl alcohol, arachidonic alcohol, behenyl alcohol, isobehenyl alcohol, selachyl alcohol, chimyl alcohol, and linoleyl alcohol and the like and mixtures thereof.

Other embodiments of the invention include dicarboxylic acid compounds containing electron withdrawing groups, alkyl esters of dicarboxylic acids containing electron withdrawing groups, or compounds of Formulae I to X prepared as described above which are formulated as a solid dosage form for oral administration including capsules, tablets, pills, powders, and granules. In such embodiments, the active compound may be admixed with one or more inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents and can additionally be prepared with enteric coatings.

Preparation of a dicarboxylic acid compound containing electron withdrawing groups, an alkyl ester of dicarboxylic acid containing electron withdrawing groups, or a compound of Formulae I to X in solid dosage form may vary. For example, in one embodiment, a liquid or gelatin formulation of a dicarboxylic acid compound containing electron withdrawing groups, an alkyl ester of dicarboxylic acid containing electron withdrawing groups, or a compound of Formulae I to X may be prepared by combining the dicarboxylic acid compound containing electron withdrawing groups, the alkyl ester of dicarboxylic acid containing electron withdrawing groups, or the compound of Formulae I to X with one or more fatty acid diluent, such as those described above, and adding a thickening agent to the liquid mixture to form a gelatin. The gelatin may then be encapsulated in unit dosage form to form a capsule. In another exemplary embodiment, an oily preparation of a dicarboxylic acid compound containing electron withdrawing groups, an alkyl ester of dicarboxylic acid containing electron withdrawing groups, or a compound of Formulae I to X prepared as described above may be lyophilized to for a solid that may be mixed with one or more pharmaceutically acceptable excipient, carrier or diluent to form a tablet, and in yet another embodiment, the dicarboxylic acid compound containing electron withdrawing groups, the alkyl ester of dicarboxylic acid containing electron withdrawing groups, or the compound of Formulae I to X of an oily preparation may be crystallized to from a solid which may be combined with a pharmaceutically acceptable excipient, carrier or diluent to form a tablet.

Further embodiments which may be useful for oral administration of the dicarboxylic acid compound containing electron withdrawing groups, the alkyl ester of dicarboxylic acid containing electron withdrawing groups, or the compound of Formulae I to X include liquid dosage forms. In such embodiments, a liquid dosage may include a pharmaceutically acceptable emulsion, solution, suspension, syrup, and elixir containing inert diluents commonly used in the art, such as water. Such compositions may also comprise adjuvants, such as wetting agents, emulsifying and suspending agents, and sweetening, flavoring, and perfuming agents.

In still further embodiments, the dicarboxylic acid compound containing electron withdrawing groups, the alkyl ester of dicarboxylic acid containing electron withdrawing groups, or the compound of Formulae I to X of the invention can be formulated as a depot preparation. Such long acting formulations can be administered by implantation (for example, subcutaneously or intramuscularly) or by intramuscular injection. Depot injections can be administered at about 1 to about 6 months or longer intervals. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Other suitable diluents for injectable formulations include, but are not limited to those described below:

Vegetable oil: As used herein, the term "vegetable oil" refers to a compound, or mixture of compounds, formed from ethoxylation of vegetable oil, wherein at least one chain of polyethylene glycol is covalently bound to the vegetable oil. In some embodiments, the fatty acids has between about twelve carbons to about eighteen carbons. In some embodiments, the amount of ethoxylation can vary from about 2 to about 200, about 5 to 100, about 10 to about 80, about 20 to about 60, or about 12 to about 18 of ethylene glycol repeat units. The vegetable oil may be hydrogenated or unhydrogenated. Suitable vegetable oils include, but are not limited to castor oil, hydrogenated castor oil, sesame oil, corn oil, peanut oil, olive oil, sunflower oil, safflower oil, soybean oil, benzyl benzoate, sesame oil, cottonseed oil, and palm oil. Other suitable vegetable oils include commercially available synthetic oils such as, but not limited to, Miglyol™ 810 and 812 (available from Dynamit Nobel Chemicals, Sweden) Neobee™ M5 (available from Drew Chemical Corp.), Alofine™ (available from Jarchem Industries), the Lubritab™ series (available from JRS Pharma), the Sterotex™ (available from Abitec Corp.), Softisan™ 154 (available from Sasol), Croduret™ (available from Croda), Fancol™ (available from the Fanning Corp.), Cutina™ HR (available from Cognis), Simulsol™ (available from CJ Petrow), EmCon™ CO (available from Amisol Co.), Lipvol™ CO, SES, and HS-K (available from Lipo), and Sterotex™ HM (available from Abitec Corp.). Other suitable vegetable oils, including sesame, castor, corn, and cottonseed oils, include those listed in R. C. Rowe and P. J. Shesky, *Handbook of Pharmaceutical Excipients*, (2006), 5th ed., which is incorporated herein by reference in its entirety. Suitable polyethoxylated vegetable oils, include but are not limited to, Cremaphor™ EL or RH series (available from BASF), Emulphor™ EL-719 (available from Stepan products), and Emulphor™ EL-620P (available from GAF).

Mineral oils: As used herein, the term "mineral oil" refers to both unrefined and refined (light) mineral oil. Suitable mineral oils include, but are not limited to, the Avatech™ grades (available from Avatar Corp.), Drakeol™ grades (available from Penreco), Sirius™ grades (available from Shell), and the Citation™ grades (available from Avater Corp.).

Castor oils: As used herein, the term "castor oil", refers to a compound formed from the ethoxylation of castor oil, wherein at least one chain of polyethylene glycol is covalently bound to the castor oil. The castor oil may be hydrogenated or unhydrogenated. Synonyms for polyethoxylated castor oil include, but are not limited to polyoxyl castor oil, hydrogenated polyoxyl castor oil, mcrogolglyceroli ricinoleas, macrogolglyceroli hydroxystearas, polyoxyl 35 castor oil, and polyoxyl 40 hydrogenated castor oil. Suitable polyethoxylated castor oils include, but are not limited to, the Nikkol™ HCO series (available from Nikko Chemicals Co. Ltd.), such as Nikkol HCO-30, HC-40, HC-50, and HC-60 (polyethylene glycol-30 hydrogenated castor oil, polyethylene glycol-40 hydrogenated castor oil, polyethylene glycol-50 hydrogenated castor oil, and polyethylene glycol-60 hydrogenated castor oil, Emulphor™ EL-7 19 (castor oil 40 mole-ethoxylate, available from Stepan Products), the Cremophore™ series (available from BASF), which includes Cremophore RH40, RH60, and EL35 (polyethylene glycol-40 hydrogenated castor oil, polyethylene glycol-60 hydrogenated castor oil, and polyethylene glycol-35 hydrogenated castor oil, respectively), and the Emulgin® RO and HRE series (available from Cognis PharmaLine). Other suitable polyoxyethylene castor oil derivatives include those listed in R. C. Rowe and P. J. Shesky, *Handbook of Pharmaceutical Excipients*, (2006), 5th ed., which is incorporated herein by reference in its entirety.

Sterol: As used herein, the term "sterol" refers to a compound, or mixture of compounds, derived from the ethoxylation of sterol molecule. Suitable polyethoyxlated sterols include, but are not limited to, PEG-24 cholesterol ether, Solulan™ C-24 (available from Amerchol); PEG-30 cholestanol, Nikkol™ DHC (available from Nikko); Phytosterol, GENEROL™ series (available from Henkel); PEG-25 phyto sterol, Nikkol™ BPSH-25 (available from Nikko); PEG-5 soya sterol, Nikkol™ BPS-5 (available from Nikko); PEG-10 soya sterol, Nikkol™ BPS-10 (available from Nikko); PEG-20 soya sterol, Nikkol™ BPS-20 (available from Nikko); and PEG-30 soya sterol, Nikkol™ BPS-30 (available from Nikko). As used herein, the term "PEG" refers to polyethylene glycol.

Polyethylene glycol: As used herein, the term "polyethylene glycol" or "PEG" refers to a polymer containing ethylene glycol monomer units of formula —O—$CH_2$—$CH_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present invention can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to, polyethylene glycol-200, polyethylene glycol-300, polyethylene glycol-400, polyethylene glycol-600, and polyethylene glycol-900. The number following the dash in the name refers to the average molecular weight of the polymer. In some embodiments, the polyethylene glycol is polyethylene glycol-400. Suitable polyethylene glycols include, but are not limited to the Carbowax™ and Carbowax™ Sentry series (available from Dow), the Lipoxol™ series (available from Brenntag), the Lutrol™ series (available from BASF), and the Pluriol™ series (available from BASF).

Propylene glycol fatty acid ester: As used herein, the term "propylene glycol fatty acid ester" refers to an monoether or diester, or mixtures thereof, formed between propylene glycol or polypropylene glycol and a fatty acid. Fatty acids that are useful for deriving propylene glycol fatty alcohol ethers include, but are not limited to, those defined herein. In some embodiments, the monoester or diester is derived from propylene glycol. In some embodiments, the monoester or diester has about 1 to about 200 oxypropylene units. In some embodiments, the polypropylene glycol portion of the molecule has about 2 to about 100 oxypropylene units. In some embodiments, the monoester or diester has about 4 to about 50 oxypropylene units. In some embodiments, the monoester or diester has about 4 to about 30 oxypropylene units. Suitable propylene glycol fatty acid esters include, but are not limited to, propylene glycol laurates: Lauroglycol™ FCC and 90 (available from Gattefosse); propylene glycol caprylates: Capryol™ PGMC and 90 (available from Gatefosse); and propylene glycol dicaprylocaprates: Labrafac™ PG (available from Gatefosse).

Stearoyl macrogol glyceride: Stearoyl macrogol glyceride refers to a polyglycolized glyceride synthesized predominately from stearic acid or from compounds derived predominately from stearic acid, although other fatty acids or compounds derived from other fatty acids may be used in the synthesis as well. Suitable stearoyl macrogol glycerides include, but are not limited to, Gelucire® 50/13 (available from Gattefosse).

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

Exemplary excipients or carriers for use m solid and/or liquid dosage forms include, but are not limited to:

Sorbitol: Suitable sorbitols include, but are not limited to, PharmSorbidex E420 (available from Cargill), Liponic 70-NC and 76-NC (available from Lipo Chemical), Neosorb (available from Roquette), Partech SI (available from Merck), and Sorbogem (available from SPI Polyols).

Starch, sodium starch glycolate, and pregelatinized starch include, but are not limited to, those described in R. C. Rowe and P. J. Shesky, *Handbook of Pharmaceutical Excipients*, (2006), 5th ed., which is incorporated herein by reference in its entirety.

Disintegrant: The disintegrant may include one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the treatment regimen as described above may be combined with a secondary form of treatment or a secondary agent. Still further embodiments of the invention include dicarboxylic acid compounds containing electron withdrawing groups, alkyl esters of dicarboxylic acids containing electron withdrawing groups, or compounds of Formulae I to X administered in combination with other active ingredients such as, for example, adjuvants, protease inhibitors, or other compatible drugs or compounds where such combination is seen to be desirable or advantageous in achieving the desired effects of the methods described herein.

In further embodiments, an activated fatty acid may be prepared through the coupling of either an aldehyde or a ketone compound additionally containing a carboxylic acid protected as an ester A and a nitroalkane compound containing a carboxylic acid protected as an ester B under Henry reaction conditions. The resulting hydroxy containing compound C is protected as the acetate ester D through reaction with acetic anhydride. Saponification of the ester groups followed by acidic workup results in dehydration of the hydroxyl group to yield the desired α-nitroalkene E. Addition of an excess of alkyl thiol to the α-nitroalkene under Michael addition conditions yields the desired activated fatty acid F as illustrated in Scheme 1 below.

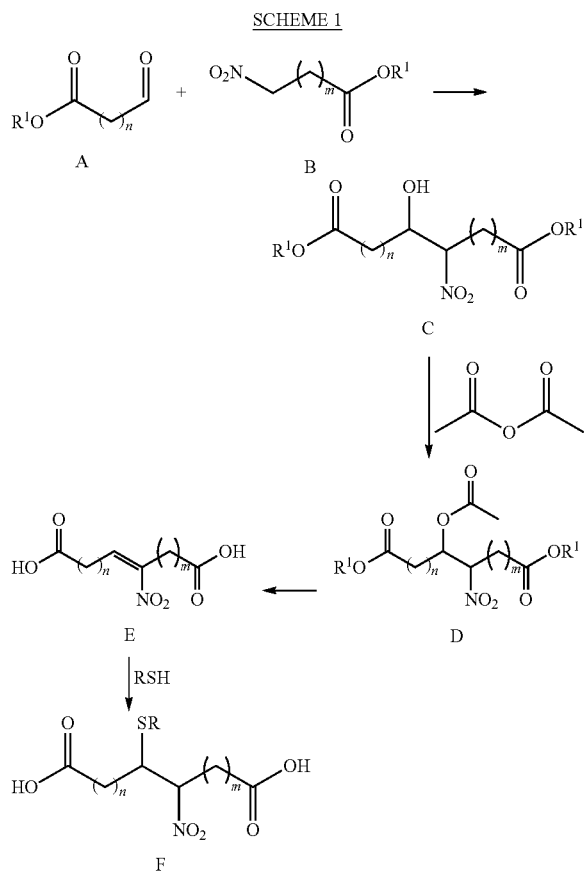

SCHEME 1

A review of the Henry reaction and methods related to the Henry method can be found, for example, in Frederick A. Luzzio, F. A. "The Henry reaction: recent examples" *Tetrahedron* 2001, 57, 915-945 which is hereby incorporated by reference in its entirety. Known variations of the Henry reaction may also be useful in preparing activated fatty acids and all such methods are embodied herein. For example, in some embodiments, variations of the Henry reaction including, but not limited to, the Wittig-like variation of the Henry reaction, the Homer-Wadsworth-Emmons variation of the Henry reaction, and the Peterson-olefination variation of the Henry reaction. In such methods, double bonds are formed using the assistance of groups temporarily included in the reactants but that do are not included in the product. For example, the Wittig reaction uses phosphorus ylides to aid in the condensation reactions with carbonyls and in the dehydration reaction to form alkenes. The Homer-Wadsworth-Emmons reaction uses phosphonate esters, and the Peterson olefination uses silicon reagents for the condensation and dehydration steps. A review of major alkene-forming name reactions by reaction of a functionalized reagent with a carbonyl compound including the Wittig reaction, Romer-Wittig, Homer-Wadsworth-Emmons can be found, for example, in Peterson, Johnson, and *Julia* reactions. Blakemore, P. R. "The modified *Julia* olefination: alkene synthesis via the condensation of metallated heteroarylalkylsulfones with carbonyl compounds *J. Chem. Soc., Perkin Trans.* 1, 2002, 2563-2585 which is hereby incorporated by reference in its entirety.

The Henry "nitro-aldol" reaction is the condensation of a nitroalkane with either an aldehyde or a ketone carbonyl containing compound to form a nitro-aldo product with the newly-formed beta-hydroxynitroalkyl group. Dehydration (loss of water) from nitro-aldol products leads to the formation of nitroalkenes. There are many methods to perform the nitroalkane-carbonyl condensation reaction to make nitro-aldols and there are many methods for the dehydration reaction to form nitroalkenes. Examples of such methods can be found in, for example, Woodcock, S. R.; Marwitz, A. J. V. Bruno, P.; Branchaud, B. P. "Synthesis of Nitrolipids. All Four Possible Diastereomers of Nitrooleic Acids: (E)- and (Z)-, 9- and 10-Nitrooctadec-9-enoic Acids" *Organic Letters,* 2006, 8, 3931-3934 which provides one regioisomer and usually one of two possible alkene cis/trans or Z/E diastereomers, in high purity and usually in high chemical yield, which is hereby incorporated by reference in its entireties.

Enantioselective Henry reactions are also possible and may require the use of one or more catalysts for the reaction, and embodiments of the invention, include the use of such methods to prepare stereospecific isomers of nitroalkenes. For example, Boruwa, J.; Gogoi, N.; Saikia, P. P.; and Barua, N. C. "Catalytic Asymmetric Henry Reaction" *Tetrahedron: Asymmetry* 2006, 17, 3315-3326 which is hereby incorporated by reference in its entirety, describes methods for preparing stereospecific isomers of nitroalkenes.

The Michael reaction or Michael addition is the nucleophilic addition of a carbanion or another nucleophile to an α,β-unsaturated carbonyl compound. It belongs to the larger class of conjugate additions. This is one of the most useful methods for the mild formation of carbon-carbon bonds. Many asymmetric variants exist. The substituent on the activated alkene, also called a Michael acceptor, is usually a ketone making it an enone; however, the substituent can also be a nitro group. As originally defined by Arthur Michael, the reaction is the addition of an enolate of a ketone or aldehyde to an α,β-unsaturated carbonyl compound at the β carbon. A newer definition, proposed by Kohler, is the 1,4-addition of a doubly stabilized carbon nucleophile to an α,β-unsaturated carbonyl compound. Some examples of nucleophiles include beta-ketoesters, malonates, and beta-cyanoesters. The resulting product contains a highly useful 1,5-dioxygenated pattern. Classical examples of the Michael reaction are the reaction between diethyl malonate (Michael donor) and diethyl fumarate (Michael acceptor), the reaction between mesityl oxide and diethyl malonate, the reaction between diethyl malonate and methyl crotonate, the reaction between 2-nitropropane and methyl acrylate, the reaction between ethyl phenylcyanoacetate and acrylonitrile, and the reaction between nitropropane and methyl vinyl ketone. The Michael addition is an important atom-economical method for diastereoselective and enantioselective carbon-carbon bond formation.

The invention claimed is:
1. A compound comprising a dicarboxylic acid having the structure:

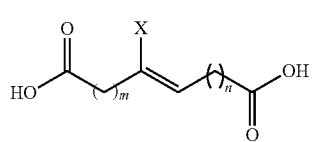

wherein X is acyl, carboxylic acid, an ester, a halogen, fluoromethyl, —CN, sulfonyl, sulfone, sulfonic acid, primary ammonium, secondary ammonium, tertiary ammonium, or –$NO_2$, m is from 1 to 10; and n is from 1 to 10.

2. A compound comprising a dicarboxylic acid having the structure:

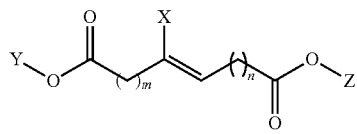

wherein X is acyl, carboxylic acid, an ester, a halogen, fluoromethyl, —CN, sulfonyl, sulfone, sulfonic acid, primary ammonium, secondary ammonium, tertiary ammonium, or —$NO_2$;

Y and Z are each, independently, hydrogen or a $C_1$ to $C_{10}$ alkyl;

m is from 1 to 10; and n is from 1 to 10.

3. A compound comprising a dicarboxylic acid having the structure:

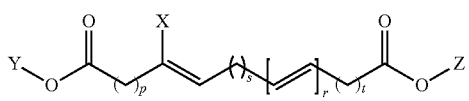

wherein X is an electron withdrawing group;

Y and Z are each, independently, hydrogen or $C_1$ to $C_{10}$ alkyl;

p and t are each, independently, 1 to 10;

s is absent or 1 to 10, and r is 1.

4. A pharmaceutical composition comprising a therapeutically effective amount of a compound selected from a compound of Formulae III, VII or IX, and a pharmaceutically acceptable excipient, wherein Formulae III, VII or IX are:

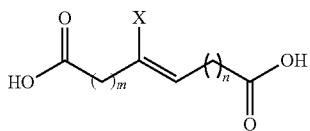
(Formula III)

wherein X is an electron withdrawing group, m is from 1 to 10; and n is from 1 to 10;

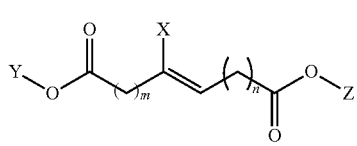
(Formula VII)

wherein X is an electron withdrawing group;

Y and Z are each, independently, hydrogen or a $C_1$ to $C_{10}$ alkyl;

m is from 1 to 10; and n is from 1 to 10;

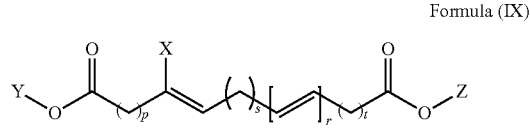
Formula (IX)

wherein X is an electron withdrawing group;

Y and Z are each, independently, hydrogen or $C_1$ to $C_{10}$ alkyl;

p and t are each, independently, 1 to 10;

s is absent or 1 to 10, and r is 1 to 5.

5. The composition of claim 4, wherein said therapeutically effective amount is from about 25 milligrams to less than 450 milligrams.

6. The composition of claim 4, wherein said therapeutically effective amount is from about 100 milligrams to about 300 milligrams.

7. The composition of claim 4, wherein said therapeutically effective amount is from about 100 milligrams to about 200 milligrams.

8. The composition of claim 4, wherein said therapeutically effective amount is about 150 milligrams.

9. The compound of claim 1, wherein X is $NO_2$.

10. The compound of claim 2, wherein X is $NO_2$.

11. The compound of claim 3, wherein X is $NO_2$.

12. The compound of claim 1, wherein m is 2 and n is 1.

13. The compound of claim 2, wherein m is 2 and n is 1.

14. The compound of claim 2, wherein Y is a $C_1$-$C_3$ alkyl and Z is a $C_1$-$C_3$ alkyl.

15. The compound of claim 10, wherein Y is a $C_1$-$C_3$ alkyl and Z is a $C_1$-$C_3$ alkyl.

16. The compound of claim 2, wherein Y is ethyl or methyl and Z is ethyl or methyl.

17. The compound of claim 10, wherein Y is ethyl or methyl and Z is ethyl or methyl.

18. The compound of claim 1, wherein X is CN.

19. The compound of claim 2, wherein X is CN.

20. The compound of claim 3, wherein X is CN.

21. The compound of claim 1, wherein X is Cl, Br or F.

22. The compound of claim 1, wherein X is Cl, Br or F.

23. The compound of claim 3, wherein X is Cl, Br or F.

24. The compound of claim 12, wherein X is $NO_2$.

25. The composition of claim 4, wherein X is $NO_2$ in Formulae III, VII or IX.

26. The composition of claim 4, wherein X is CN in Formulae III, VII or IX.

27. The composition of claim 4, wherein X is Cl, Br or F in Formulae III, VII or IX.

28. The composition of claim 4, wherein m is 2 and n is 1 in Formulae III or VII.

29. The composition of claim 4, wherein Y is a $C_1$-$C_3$ alkyl and Z is a $C_1$-$C_3$ alkyl in Formulae VII or IX.

30. The composition of claim 4, wherein Y is ethyl or methyl and Z is ethyl or methyl in Formulae VII or IX.

31. The composition of claim 4, wherein the compound is a compound of Formulae III.

32. The composition of claim 4, wherein the compound is a compound of Formulae VII.

33. The composition of claim 4, wherein the compound is a compound of Formulae IX.

34. The composition of claim 4, wherein X is acyl, carboxylic acid, an ester, a halogen, fluoromethyl, —CN, sulfonyl, sulfone, sulfonic acid, primary ammonium, secondary ammonium, tertiary ammonium, or —NO$_2$ in Formulae III, VII or IX.

35. The composition of claim 25, wherein the compound is a compound of Formulae III.

36. The composition of claim 25, wherein the compound is a compound of Formulae VII.

37. The composition of claim 25, wherein the compound is a compound of Formulae IX.

* * * * *